United States Patent
Fukui (10) Patent No.: US 8,441,636 B2
(45) Date of Patent: May 14, 2013

(54) NANOPARTICLE DETECTOR

(75) Inventor: Toshimi Fukui, Ohtsu (JP)

(73) Assignee: Empire Technology Development LLC, Wilmington, DE (US)

( * ) Notice: Subject to any disclaimer, the term of this patent is extended or adjusted under 35 U.S.C. 154(b) by 41 days.

(21) Appl. No.: 13/201,124

(22) PCT Filed: Nov. 1, 2010

(86) PCT No.: PCT/US2010/054938
§ 371 (c)(1),
(2), (4) Date: Aug. 11, 2011

(87) PCT Pub. No.: WO2012/060809
PCT Pub. Date: May 10, 2012

(65) Prior Publication Data
US 2012/0105848 A1    May 3, 2012

(51) Int. Cl.
*G01N 15/02* (2006.01)
*G01N 21/00* (2006.01)

(52) U.S. Cl.
USPC ........... 356/336; 356/335; 356/337; 356/338; 356/432

(58) Field of Classification Search .......... 356/335–343, 356/301, 317, 328, 73; 250/458.1, 287; 436/171; 977/773, 880; 378/88, 86
See application file for complete search history.

(56) References Cited

U.S. PATENT DOCUMENTS

| 4,693,602 | A | 9/1987 | Wyatt et al. |
| 5,561,515 | A | 10/1996 | Hairston et al. |
| 6,981,897 | B2 * | 1/2006 | Sakatani ................... 439/606 |
| 2004/0142484 | A1 * | 7/2004 | Berlin et al. ............... 436/171 |
| 2007/0188749 | A1 * | 8/2007 | Brady et al. ............... 356/301 |
| 2009/0213372 | A1 | 8/2009 | Kovalenko et al. |
| 2010/0285989 | A1 * | 11/2010 | Huo et al. ................... 506/9 |
| 2011/0135061 | A1 * | 6/2011 | Thunemann ............... 378/88 |
| 2011/0214991 | A1 * | 9/2011 | Kim et al. ................. 204/452 |
| 2012/0050736 | A1 * | 3/2012 | Strong et al. ............. 356/337 |

FOREIGN PATENT DOCUMENTS
WO    WO-2006/137090    12/2006

OTHER PUBLICATIONS

Bohren, C.F. et al., "Particles Small Compared with the Wavelength," in Wiley *Absorption and scattering of light by small particles*, 1998, p. 132.
Carr, B., "Real-time nanoparticle detection and analysis on a particle-by-particle basis," SPIE Newsroom, Jul. 22, 2009, printed on Jun. 7, 2011, retrieved from the internet (http://spie.org/x38118.xml?pf=true&ArticleID=x38118), 4 pages.
Freud, P., "Nanoparticle Sizing: Dynamic Light Scattering Analysis in the Frequency Spectrum Mode," Microtrac Inc., Jul. 19, 2007, 7 pages.

(Continued)

*Primary Examiner* — Sang Nguyen
(74) *Attorney, Agent, or Firm* — Foley & Lardner LLP (57) ABSTRACT

The present technology provides a nanoparticle detector that includes a nanoparticle collector that is configured to collect a volume of air that includes nanoparticles and a light source that is configured to transmit light through the volume of air. The nanoparticle detector further includes a first light-receiving element that is configured to receive at least a portion of the transmitted light and to detect characteristics of the nanoparticles within the volume of air based on scattering properties of the transmitted light.

20 Claims, 4 Drawing Sheets

OTHER PUBLICATIONS

Fujitani Y. et al., "Health Effects of Nanoparticles and Nanomaterials (II) Methods for MEasurement of Nanoparticles and Their Presence in the Air," Jpn. J. Hyg., 2008, vol. 63, pp. 663-669 (with English Abstract).

Otsuka Electronics Co., "3. The principle of dynamic light scattering," printed on Jul. 28, 2011, retrieved from the internet (http://translate.google.com/translate?js=n&prev=_t&hl=en&ie=UTF-8&layout=2&eotf=1&sl=auto&tl=en&u=http%3A%2F%2Fwww.photal.co.jp%2Fbook%2Fbe_01_00.html&act=url), 4 pages.

Otsuka Electronics Co., "5. The principle of dynamic light scattering analysis," printed on Jul. 28, 2011, retrieved from the internet (http://translate.google.com/translate?hl=en&st=auto&tl=en&u=http%3A%2F%2Fwww.photal.co.jp%2Fbook%2Fbe_01_05.html), 3 pages.

Ignatovich, F.V. et al., "Real-time and Background-free detection of Nanoscale Particles," Physical Review Letters, Jan. 13, 2006, vol. 96, pp. 013901-1-013901-4.

International Search Report and Written Opinion for PCT/US2010/054938 mailed Jan. 28, 2011.

Xu, R., "4.2.2. Optics of the Volumetric Instrument" in Kulwer Academic Publishers, *Particle Characterization: Light Scattering Methods*, 2002, pp. 186-189.

\* cited by examiner

FIG. 4

NANOPARTICLE DETECTOR

CROSS-REFERENCE TO RELATED APPLICATIONS

The present application is a U.S. national stage application claiming the benefit of International Application No. PCT/US2010/054938, filed on Nov. 1, 2010, the entire contents of which is incorporated herein by reference in its entirety.

BACKGROUND

The following description is provided to assist the understanding of the reader. None of the information provided or references cited is admitted to be prior art.

Harmful particles and pollutants are commonly found in the air not only in industrial and laboratory settings, but also in everyday living spaces of the public. Accordingly, many countries, municipalities, and governments mandate specific monitoring and air quality reporting to increase awareness and safety for the public. In industrial settings, monitoring and treatment of air pollution may be required for the safety of workers involved in activities that produce hazardous materials or that involve such hazardous materials. Monitoring of air pollutants also has substantial personal application; for example, in individual homes for the detection of carbon monoxide and by individuals in the event of a chemical or biological terrorist attack.

Traditional detection systems for such harmful particles and pollutants have generally been designed for use in industrial and laboratory settings, and, as such, have traditionally been very expensive and large in size. More affordable air monitoring devices having small sizes and increased efficiencies are much more advantageous to more expensive devices having larger sizes and greater inefficiencies. Compact device sizes allow for the use of monitoring devices in applications that will not allow for large device sizes. For example, placement of monitoring devices in small spaces and inclusion of monitoring devices on personal safety equipment having limited space. Efficient monitoring devices allow for faster analysis of air pollutants and lead to faster notification of pollutant levels. However, small monitoring devices have traditionally been inferior to conventional large monitoring equipment in terms of accuracy and sensitivity. In addition, traditional monitoring equipment is often quite expensive rendering widespread use by individuals impractical.

SUMMARY

The present technology provides an illustrative method for optically detecting nanoparticles that includes collecting air in a nanoparticle collector and transmitting light through the collected air using a light source. The method further includes receiving at least a portion of the transmitted light at a first light-receiving element and detecting characteristics of particles within the air based on scattering properties of the transmitted light.

The present technology further provides an illustrative nanoparticle detector that includes a nanoparticle collector that is configured to collect a volume of air that includes particles and a light source that is configured to transmit light through the collected volume of air. The illustrative nanoparticle detector further includes a first light-receiving element that is configured to receive at least a portion of the transmitted light and to detect characteristics of the particles within the collected volume of air based on scattering properties of the transmitted light.

The present technology also includes another illustrative nanoparticle detector that includes means for collecting air and means for transmitting a light through the collected air. The illustrative nanoparticle detector further includes means for receiving the transmitted light and means for detecting characteristics of particles within the collected air based on scattering properties of the transmitted light.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

There are a variety of issues associated with traditional air pollutant monitors. These include, but are not limited to, the traditionally large size and complexity of such monitors and the associated expense of traditional air monitors. In addition, the large size and greater complexity of traditional air monitors have limited the portability of such monitors. Smaller, more portable air monitors have often suffered from lower efficiency and sensitivity than larger, more complex monitors. Described herein are illustrative systems for monitoring particles within the air using cost-effective, compact, sensitive, and efficient monitoring devices. The monitoring devices collect air containing various particles, emit a light through the collected air, and detect the size and concentrations of the particles in the collected air based on the scattering properties of the emitted light. The monitoring devices and methods described below allow for increasing sensitivity and efficiency while decreasing the size and expense of the associated monitoring device.

Figure 1:
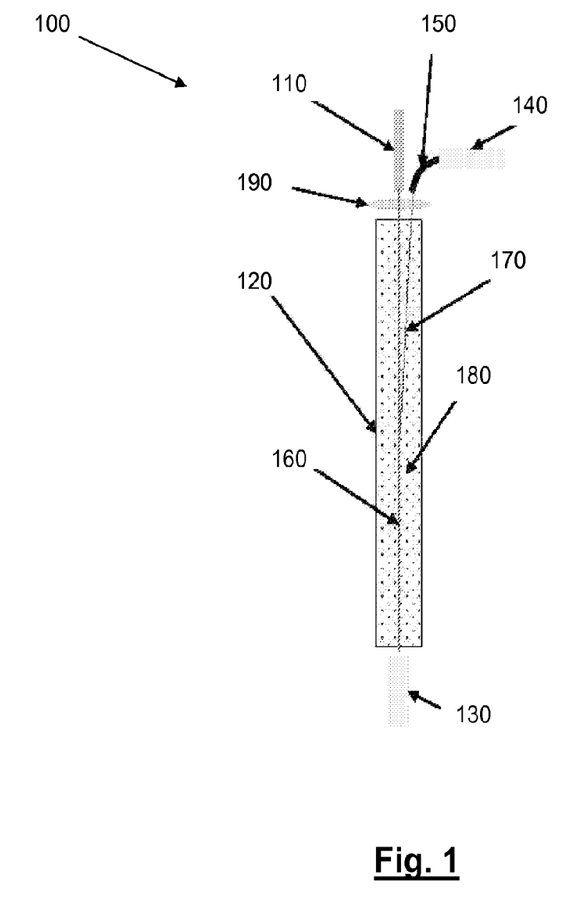
FIG. 1 depicts a nanoparticle monitoring device in accordance with an illustrative embodiment.

FIG. 1 depicts a nanoparticle monitoring device 100 in accordance with an illustrative embodiment. Nanoparticle monitoring device 100 includes a light source 110 that is configured to transmit incident light 160 through a volume of air collected in a collector 120. In one example embodiment, light source 110 is a semiconductor laser that outputs a light having a wavelength of 660 nm, 589 nm, 468 nm, 440 nm, or 45 nm. In alternative embodiments, light source 110 may produce light at alternative wavelengths and light source 110 may produce any kind of light that can retain its directionality. In one possible embodiment, a laser capable of emitting visible light may be used. For example, the laser may be a yttrium aluminum garnet (YAG) laser, a helium-neon (He—Ne) laser, an argon-ion laser, or any other semiconductor laser known to those of skill in the art. Smaller wavelengths allow for greater detection of scattered light to be achieved, thus enhancing the sensitivity and accuracy of the monitoring device.

Air may be moved into and out of the collector via any process or device known to those of skill in the art such a pump or a fan. For example, according to a first embodiment, a pump or a fan may be located near a first light receiving element 130 and may be configured to move air into and out of the device. According to such an embodiment, the pump or fan may be stopped when a measurement is being performed to maintain a constant number of particles within collector 120 during the measurement. In alternative embodiments, the measurements of the particles are done without stopping the pump or fan, thus allowing for real-time monitoring.

The air in collector 120 includes particles 180. As incident light 160 is transmitted through the collected air in collector 120, some light 170 is backscattered as it contacts particles 180. The diameter of incident light 160 may range from several microns to 10 millimeters. In an embodiment, collector 120 has a diameter that is several times larger than the diameter of the transmitted incident light 160 in order to ensure the light does not contact the surface of collector 120. As such, according to one embodiment, the collector 120 has a diameter that is larger than the diameter of incident light 160 and a length that is sufficient to enable the measurement of transmitted light attenuation due to scattering by particles 180. The appropriate length of collector 120 depends on the minimum particle size for which monitoring device 100 is designed to detect. For example, in an embodiment collector 120 has a diameter of 10 cm and a length of 350 cm in order to detect particles having a minimum diameter of 5 nm.

A first light-receiving element 130 receives incident light 160 that successfully passes through the air collected in collector 120. In an embodiment, first light-receiving element 130 is located on a surface of collector 120. In an alternative embodiment, first light-receiving element 130 may be located outside of collector 120 and may receive the transmitted incident light 160 after it has passed entirely through collector 120. A second light-receiving element 140 receives backscattered light 170. An optical fiber 150 captures backscattered light 170 and provides an optical path by which backscattered light 170 is transmitted to light-receiving element 140. In an alternative embodiment, second light-receiving element 140 is located at a surface of collector 120 and nanoparticle monitoring device 100 includes a prism configured to change the light path of backscattered light to direct it second light-receiving element 140. According to such an embodiment, optical fiber 150 is not included in nanoparticle monitoring device 100.

In an embodiment, light-receiving element 130 and light-receiving element 140 comprise an avalanche photodiode or a charge-coupled device. Nanoparticle monitoring device 100 further includes a lens 190 that is configured to increase the intensity of backscattered light 170 prior to reception of the backscattered light at light-receiving element 140.

The amount of incident light 160 and backscattered light 170 received at light-receiving elements 130 and 140 is used to determine the sizes of particles 180 based on a dynamic light scattering profile determined from an amount of backscattered light 170, and to determine a concentration of particles 180 based on an attenuation factor of incident light 160. A Raleigh scattering model as shown below is used to construct the dynamic light scattering profile and to calculate the sizes and concentration of particles 180:

$$C_{sca} = \frac{8}{3}\left(\frac{2\pi n_p r}{\lambda}\right)^4 \left(\frac{\left(\frac{n_p}{n_m}\right)^2 - 1}{\left(\frac{n_p}{n_m}\right)^2 + 2}\right)^2 * \pi r^2 \quad \text{Eqn. 1}$$

$$\alpha_{sca} = \frac{3\eta C_{sca}}{4\pi r^3} \quad \text{Eqn. 2}$$

where $C_{sca}$ is the scattering cross-section; $n_m$ is the refractive index of the host material; $n_p$ is the refractive index of inclusion; r is the radius of inclusion; $\lambda$ is the wavelength of the propagating light; $\alpha_{sca}$ is the extinction coefficient; and $\eta$ is the volume fraction of inclusions. The transmittance of incident light 160, i.e., the fraction of incident light passed through collector 120, is determined according to the following equation:

$T = e^{-C_{sca}*d}$; where T is the transmittance and where d is the length of collector 120.

In an embodiment, a computing device is communicatively coupled to nanoparticle monitoring device 100 in order to receive data from nanoparticle monitoring device 100 and perform calculations based on Equations 1 and 2 above. For example, the computing device may be communicatively coupled to at least one of light-receiving elements 130 and 140 in order to receive data from light-receiving elements 130 and 140. The computing device may then implement Equations 1 and 2 above in order to determine values for one or more of the variables associated with Equations 1 and 2 based on the received data. For example, in an embodiment, the computing device may be configured to calculate the transmittance of incident light 160 and the concentration and/or size of particles 180 based on data received from light-receiving elements 130 and 140.

In an embodiment, the computing device includes a processor, a communication interface, and a computer-readable medium configured to store instructions to be executed by the processor as known to those of skill in the art. The processor is configured to execute the stored instructions to perform the calculations and to store and/or communicate data associated with the calculations. The computing device may further be coupled to a display device, as known to those of skill in the art.

Below Charts 1, 2, and 3 are presented. Charts 1, 2, and 3 show example values for these variables according to various embodiments having a collector length of about 350 cm where r is the radius of an average particle to be detected from the volume of air and d is the diameter of the average particle to be detected in the volume of air. Chart 1 depicts values of the variables according to several embodiments as the transmittance is varied and the average size of the particles is held constant. Chart 2 depicts values of the variables according to several embodiments as the average size of the particles is varied. Chart 3 depicts values of the variables according to several embodiments as the wavelength of the propagated light is varied.

CHART 1

| η (particle volume fraction) | α$_{sca}$ (cm$^{-1}$) | Transmittance/mm | C$_{sca}$ (cm$^2$) | n$_p$ | n$_m$ | r (mm) | d (mm) | λ (μm) |
|---|---|---|---|---|---|---|---|---|
| 0.0E+00 | 0.00E+00 | 1 | 1.160E-19 | 1.5 | 1 | 2.5 | 5 | 0.589 |
| 1.0E-05 | 1.77E-05 | 0.9938165 | 1.160E-19 | 1.5 | 1 | 2.5 | 5 | 0.589 |
| 2.0E-05 | 3.54E-05 | 0.9876712 | 1.160E-19 | 1.5 | 1 | 2.5 | 5 | 0.589 |
| 3.0E-05 | 5.32E-05 | 0.9815638 | 1.160E-19 | 1.5 | 1 | 2.5 | 5 | 0.589 |
| 4.0E-05 | 7.09E-05 | 0.9754943 | 1.160E-19 | 1.5 | 1 | 2.5 | 5 | 0.589 |
| 5.0E-05 | 8.86E-05 | 0.9694623 | 1.160E-19 | 1.5 | 1 | 2.5 | 5 | 0.589 |
| 6.0E-05 | 1.06E-04 | 0.9634676 | 1.160E-19 | 1.5 | 1 | 2.5 | 5 | 0.589 |
| 7.0E-05 | 1.24E-04 | 0.9575099 | 1.160E-19 | 1.5 | 1 | 2.5 | 5 | 0.589 |
| 8.0E-05 | 1.42E-04 | 0.9515891 | 1.160E-19 | 1.5 | 1 | 2.5 | 5 | 0.589 |
| 9.0E-05 | 1.59E-04 | 0.9457049 | 1.160E-19 | 1.5 | 1 | 2.5 | 5 | 0.589 |
| 1.0E-04 | 1.77E-04 | 0.9398571 | 1.160E-19 | 1.5 | 1 | 2.5 | 5 | 0.589 |
|  |  |  |  |  |  |  |  | 0.589 |
| 0.0E+00 | 0.00E+00 | 1 | 7.423E-18 | 1.5 | 1 | 5 | 10 | 0.589 |
| 1.0E-05 | 1.42E-04 | 0.9515891 | 7.423E-18 | 1.5 | 1 | 5 | 10 | 0.589 |
| 2.0E-05 | 2.84E-04 | 0.9055219 | 7.423E-18 | 1.5 | 1 | 5 | 10 | 0.589 |
| 3.0E-05 | 4.25E-04 | 0.8616848 | 7.423E-18 | 1.5 | 1 | 5 | 10 | 0.589 |
| 4.0E-05 | 5.67E-04 | 0.8199699 | 7.423E-18 | 1.5 | 1 | 5 | 10 | 0.589 |
| 5.0E-05 | 7.09E-04 | 0.7802744 | 7.423E-18 | 1.5 | 1 | 5 | 10 | 0.589 |
| 6.0E-05 | 8.51E-04 | 0.7425007 | 7.423E-18 | 1.5 | 1 | 5 | 10 | 0.589 |
| 7.0E-05 | 9.92E-04 | 0.7065556 | 7.423E-18 | 1.5 | 1 | 5 | 10 | 0.589 |
| 8.0E-05 | 1.13E-03 | 0.6723506 | 7.423E-18 | 1.5 | 1 | 5 | 10 | 0.589 |
| 9.0E-05 | 1.28E-03 | 0.6398015 | 7.423E-18 | 1.5 | 1 | 5 | 10 | 0.589 |
| 1.0E-04 | 1.42E-03 | 0.6088282 | 7.423E-18 | 1.5 | 1 | 5 | 10 | 0.589 |
|  |  |  |  |  |  |  |  | 0.589 |
| 0.0E+00 | 0.00E+00 | 1 | 4.751E-16 | 1.5 | 1 | 10 | 20 | 0.589 |
| 1.0E-05 | 1.13E-03 | 0.6723506 | 4.751E-16 | 1.5 | 1 | 10 | 20 | 0.589 |
| 2.0E-05 | 2.27E-03 | 0.4520553 | 4.751E-16 | 1.5 | 1 | 10 | 20 | 0.589 |
| 3.0E-05 | 3.40E-03 | 0.3039397 | 4.751E-16 | 1.5 | 1 | 10 | 20 | 0.589 |
| 4.0E-05 | 4.54E-03 | 0.204354 | 4.751E-16 | 1.5 | 1 | 10 | 20 | 0.589 |
| 5.0E-05 | 5.67E-03 | 0.1373975 | 4.751E-16 | 1.5 | 1 | 10 | 20 | 0.589 |
| 6.0E-05 | 6.81E-03 | 0.0923793 | 4.751E-16 | 1.5 | 1 | 10 | 20 | 0.589 |
| 7.0E-05 | 7.94E-03 | 0.0621113 | 4.751E-16 | 1.5 | 1 | 10 | 20 | 0.589 |
| 8.0E-05 | 9.07E-03 | 0.0417606 | 4.751E-16 | 1.5 | 1 | 10 | 20 | 0.589 |
| 9.0E-05 | 1.02E-02 | 0.0280777 | 4.751E-16 | 1.5 | 1 | 10 | 20 | 0.589 |
| 1.0E-04 | 1.13E-02 | 0.0188781 | 4.751E-16 | 1.5 | 1 | 10 | 20 | 0.589 |

CHART 2

| η (particle volume fraction) | α$_{sca}$ (cm$^{-1}$) | Transmittance/mm | C$_{sca}$ (cm$^2$) | n$_p$ | n$_m$ | r (mm) | d (mm) | λ (μm) |
|---|---|---|---|---|---|---|---|---|
| 1.0E-12 | 1.13E-19 | 1 | 4.751E-34 | 1.5 | 1 | 0.01 | 0.02 | 0.589 |
| 1.0E-12 | 1.42E-11 | 1 | 7.423E-18 | 1.5 | 1 | 5 | 10 | 0.589 |
| 1.0E-12 | 1.13E-10 | 1 | 4.751E-16 | 1.5 | 1 | 10 | 20 | 0.589 |
| 1.0E-12 | 3.83E-10 | 0.9999999 | 5.412E-15 | 1.5 | 1 | 15 | 30 | 0.589 |
| 1.0E-12 | 9.07E-10 | 0.9999997 | 3.041E-14 | 1.5 | 1 | 20 | 40 | 0.589 |
| 1.0E-12 | 1.77E-09 | 0.9999994 | 1.160E-13 | 1.5 | 1 | 25 | 50 | 0.589 |
| 1.0E-12 | 3.06E-09 | 0.9999989 | 3.463E-13 | 1.5 | 1 | 30 | 60 | 0.589 |
| 1.0E-12 | 4.86E-09 | 0.9999983 | 8.734E-13 | 1.5 | 1 | 35 | 70 | 0.589 |
| 1.0E-12 | 7.26E-09 | 0.9999975 | 1.946E-12 | 1.5 | 1 | 40 | 80 | 0.589 |
| 1.0E-12 | 1.03E-08 | 0.9999964 | 3.945E-12 | 1.5 | 1 | 45 | 90 | 0.589 |
| 1.0E-12 | 1.42E-08 | 0.999995 | 7.423E-12 | 1.5 | 1 | 50 | 100 | 0.589 |
|  |  |  |  |  |  |  |  | 0.589 |
| 1.0E-10 | 1.13E-17 | 1 | 4.751E-34 | 1.5 | 1 | 0.01 | 0.02 | 0.589 |
| 1.0E-10 | 1.42E-09 | 0.9999995 | 7.423E-18 | 1.5 | 1 | 5 | 10 | 0.589 |
| 1.0E-10 | 1.13E-08 | 0.999996 | 4.751E-16 | 1.5 | 1 | 10 | 20 | 0.589 |
| 1.0E-10 | 3.83E-08 | 0.9999866 | 5.412E-15 | 1.5 | 1 | 15 | 30 | 0.589 |
| 1.0E-10 | 9.07E-08 | 0.9999682 | 3.041E-14 | 1.5 | 1 | 20 | 40 | 0.589 |
| 1.0E-10 | 1.77E-07 | 0.999938 | 1.160E-13 | 1.5 | 1 | 25 | 50 | 0.589 |
| 1.0E-10 | 3.06E-07 | 0.9998928 | 3.463E-13 | 1.5 | 1 | 30 | 60 | 0.589 |
| 1.0E-10 | 4.86E-07 | 0.9998298 | 8.734E-13 | 1.5 | 1 | 35 | 70 | 0.589 |
| 1.0E-10 | 7.26E-07 | 0.999746 | 1.946E-12 | 1.5 | 1 | 40 | 80 | 0.589 |
| 1.0E-10 | 1.03E-06 | 0.9996383 | 3.945E-12 | 1.5 | 1 | 45 | 90 | 0.589 |
| 1.0E-10 | 1.42E-06 | 0.9995039 | 7.423E-12 | 1.5 | 1 | 50 | 100 | 0.589 |
|  |  |  |  |  |  |  |  | 0.589 |
| 1.0E-09 | 1.13E-16 | 1 | 4.751E-34 | 1.5 | 1 | 0.01 | 0.02 | 0.589 |
| 1.0E-09 | 1.42E-08 | 0.999995 | 7.423E-18 | 1.5 | 1 | 5 | 10 | 0.589 |
| 1.0E-09 | 1.13E-07 | 0.9999603 | 4.751E-16 | 1.5 | 1 | 10 | 20 | 0.589 |
| 1.0E-09 | 3.83E-07 | 0.999866 | 5.412E-15 | 1.5 | 1 | 15 | 30 | 0.589 |
| 1.0E-09 | 9.07E-07 | 0.9996825 | 3.041E-14 | 1.5 | 1 | 20 | 40 | 0.589 |
| 1.0E-09 | 1.77E-06 | 0.9993799 | 1.160E-13 | 1.5 | 1 | 25 | 50 | 0.589 |
| 1.0E-09 | 3.06E-06 | 0.9989287 | 3.463E-13 | 1.5 | 1 | 30 | 60 | 0.589 |
| 1.0E-09 | 4.86E-06 | 0.9982994 | 8.734E-13 | 1.5 | 1 | 35 | 70 | 0.589 |

CHART 2-continued

| η (particle volume fraction) | $\alpha_{sca}$ (cm$^{-1}$) | Transmittance/mm | $C_{sca}$ (cm$^2$) | $n_p$ | $n_m$ | r (mm) | d (mm) | λ (μm) |
|---|---|---|---|---|---|---|---|---|
| 1.0E−09 | 7.26E−06 | 0.9974626 | 1.946E−12 | 1.5 | 1 | 40 | 80 | 0.589 |
| 1.0E−09 | 1.03E−05 | 0.9963891 | 3.945E−12 | 1.5 | 1 | 45 | 90 | 0.589 |
| 1.0E−09 | 1.42E−05 | 0.9950501 | 7.423E−12 | 1.5 | 1 | 50 | 100 | 0.589 |
| | | | | | | | | 0.589 |
| 1.0E−08 | 1.13E−15 | 1 | 4.751E−34 | 1.5 | 1 | 0.01 | 0.02 | 0.589 |
| 1.0E−08 | 1.42E−07 | 0.9999504 | 7.423E−18 | 1.5 | 1 | 5 | 10 | 0.589 |
| 1.0E−08 | 1.13E−06 | 0.9996031 | 4.751E−16 | 1.5 | 1 | 10 | 20 | 0.589 |
| 1.0E−08 | 3.83E−06 | 0.9986611 | 5.412E−15 | 1.5 | 1 | 15 | 30 | 0.589 |
| 1.0E−08 | 9.07E−06 | 0.9968292 | 3.041E−14 | 1.5 | 1 | 20 | 40 | 0.589 |
| 1.0E−08 | 1.77E−05 | 0.9938165 | 1.160E−13 | 1.5 | 1 | 25 | 50 | 0.589 |
| 1.0E−08 | 3.06E−05 | 0.9893389 | 3.463E−13 | 1.5 | 1 | 30 | 60 | 0.589 |
| 1.0E−08 | 4.86E−05 | 0.9831237 | 8.734E−13 | 1.5 | 1 | 35 | 70 | 0.589 |
| 1.0E−08 | 7.26E−05 | 0.9749136 | 1.946E−12 | 1.5 | 1 | 40 | 80 | 0.589 |
| 1.0E−08 | 1.03E−04 | 0.9644721 | 3.945E−12 | 1.5 | 1 | 45 | 90 | 0.589 |
| 1.0E−08 | 1.42E−04 | 0.9515891 | 7.423E−12 | 1.5 | 1 | 50 | 100 | 0.589 |

CHART 3

| η (particle volume fraction) | $\alpha_{sca}$ (cm$^{-1}$) | Transmittance/mm | $C_{sca}$ (cm$^2$) | $n_p$ | $n_m$ | r (mm) | d (mm) | λ (μm) |
|---|---|---|---|---|---|---|---|---|
| 5.0E−01 | 2.67E−01 | 2.975E−41 | 2.234E−21 | 1.5 | 1 | 1 | 2 | 0.4 |
| 5.0E−01 | 2.09E−01 | 1.586E−32 | 1.753E−21 | 1.5 | 1 | 1 | 2 | 0.425 |
| 5.0E−01 | 1.66E−01 | 5.006E−26 | 1.394E−21 | 1.5 | 1 | 1 | 2 | 0.45 |
| 5.0E−01 | 1.34E−01 | 4.169E−21 | 1.123E−21 | 1.5 | 1 | 1 | 2 | 0.475 |
| 5.0E−01 | 1.09E−01 | 2.514E−17 | 9.149E−22 | 1.5 | 1 | 1 | 2 | 0.5 |
| 5.0E−01 | 8.98E−02 | 2.205E−14 | 7.527E−22 | 1.5 | 1 | 1 | 2 | 0.525 |
| 5.0E−01 | 7.46E−02 | 4.594E−12 | 6.249E−22 | 1.5 | 1 | 1 | 2 | 0.55 |
| 5.0E−01 | 6.24E−02 | 3.229E−10 | 5.231E−22 | 1.5 | 1 | 1 | 2 | 0.575 |
| 5.0E−01 | 5.27E−02 | 9.88E−09 | 4.412E−22 | 1.5 | 1 | 1 | 2 | 0.6 |
| 5.0E−01 | 4.47E−02 | 1.588E−07 | 3.747E−22 | 1.5 | 1 | 1 | 2 | 0.625 |
| 5.0E−01 | 3.82E−02 | 1.542E−06 | 3.203E−22 | 1.5 | 1 | 1 | 2 | 0.65 |
| 5.0E−01 | 3.29E−02 | 1.005E−05 | 2.754E−22 | 1.5 | 1 | 1 | 2 | 0.675 |
| 5.0E−01 | 2.84E−02 | 4.775E−05 | 2.382E−22 | 1.5 | 1 | 1 | 2 | 0.7 |
| 5.0E−01 | 2.47E−02 | 0.0001757 | 2.070E−22 | 1.5 | 1 | 1 | 2 | 0.725 |
| 5.0E−01 | 2.16E−02 | 0.0005261 | 1.807E−22 | 1.5 | 1 | 1 | 2 | 0.75 |
| 5.0E−01 | 1.89E−02 | 0.0013308 | 1.585E−22 | 1.5 | 1 | 1 | 2 | 0.775 |
| 5.0E−01 | 1.67E−02 | 0.0029315 | 1.396E−22 | 1.5 | 1 | 1 | 2 | 0.8 |
| 5.0E−01 | 1.47E−02 | 0.0057602 | 1.234E−22 | 1.5 | 1 | 1 | 2 | 0.825 |
| 5.0E−01 | 4.17E+00 | 0 | 5.453E−19 | 1.5 | 1 | 3 | 5 | 0.4 |
| 5.0E−01 | 3.27E+00 | 0 | 4.279E−19 | 1.5 | 1 | 3 | 5 | 0.425 |
| 5.0E−01 | 2.60E+00 | 0 | 3.404E−19 | 1.5 | 1 | 3 | 5 | 0.45 |
| 5.0E−01 | 2.09E+00 | 0 | 2.742E−19 | 1.5 | 1 | 3 | 5 | 0.475 |
| 5.0E−01 | 1.71E+00 | 4.27E−260 | 2.234E−19 | 1.5 | 1 | 3 | 5 | 0.5 |
| 5.0E−01 | 1.40E+00 | 4.13E−214 | 1.838E−19 | 1.5 | 1 | 3 | 5 | 0.525 |
| 5.0E−01 | 1.17E+00 | 7.03E−178 | 1.526E−19 | 1.5 | 1 | 3 | 5 | 0.55 |
| 5.0E−01 | 9.76E−01 | 5.07E−149 | 1.277E−19 | 1.5 | 1 | 3 | 5 | 0.575 |
| 5.0E−01 | 8.23E−01 | 8.28E−126 | 1.077E−19 | 1.5 | 1 | 3 | 5 | 0.6 |
| 5.0E−01 | 6.99E−01 | 5.78E−107 | 9.149E−20 | 1.5 | 1 | 3 | 5 | 0.625 |
| 5.0E−01 | 5.97E−01 | 1.54E−91 | 7.820E−20 | 1.5 | 1 | 3 | 5 | 0.65 |
| 5.0E−01 | 5.14E−01 | 8.167E−79 | 6.725E−20 | 1.5 | 1 | 3 | 5 | 0.675 |
| 5.0E−01 | 4.44E−01 | 3.048E−68 | 5.814E−20 | 1.5 | 1 | 3 | 5 | 0.7 |
| 5.0E−01 | 3.86E−01 | 2.117E−59 | 5.053E−20 | 1.5 | 1 | 3 | 5 | 0.725 |
| 5.0E−01 | 3.37E−01 | 5.841E−52 | 4.412E−20 | 1.5 | 1 | 3 | 5 | 0.75 |
| 5.0E−01 | 2.96E−01 | 1.159E−45 | 3.870E−20 | 1.5 | 1 | 3 | 5 | 0.775 |
| 5.0E−01 | 2.60E−01 | 2.651E−40 | 3.408E−20 | 1.5 | 1 | 3 | 5 | 0.8 |
| 5.0E−01 | 2.30E−01 | 1.016E−35 | 3.013E−20 | 1.5 | 1 | 3 | 5 | 0.825 |
| 5.0E−01 | 3.33E+01 | 0 | 3.490E−17 | 1.5 | 1 | 5 | 10 | 0.4 |
| 5.0E−01 | 2.62E+01 | 0 | 2.738E−17 | 1.5 | 1 | 5 | 10 | 0.425 |
| 5.0E−01 | 2.08E+01 | 0 | 2.179E−17 | 1.5 | 1 | 5 | 10 | 0.45 |
| 5.0E−01 | 1.68E+01 | 0 | 1.755E−17 | 1.5 | 1 | 5 | 10 | 0.475 |
| 5.0E−01 | 1.37E+01 | 0 | 1.430E−17 | 1.5 | 1 | 5 | 10 | 0.5 |
| 5.0E−01 | 1.12E+01 | 0 | 1.176E−17 | 1.5 | 1 | 5 | 10 | 0.525 |
| 5.0E−01 | 9.32E+00 | 0 | 9.764E−18 | 1.5 | 1 | 5 | 10 | 0.55 |
| 5.0E−01 | 7.80E+00 | 0 | 8.173E−18 | 1.5 | 1 | 5 | 10 | 0.575 |
| 5.0E−01 | 6.58E+00 | 0 | 6.894E−18 | 1.5 | 1 | 5 | 10 | 0.6 |
| 5.0E−01 | 5.59E+00 | 0 | 5.855E−18 | 1.5 | 1 | 5 | 10 | 0.625 |
| 5.0E−01 | 4.78E+00 | 0 | 5.005E−18 | 1.5 | 1 | 5 | 10 | 0.65 |
| 5.0E−01 | 4.11E+00 | 0 | 4.304E−18 | 1.5 | 1 | 5 | 10 | 0.675 |
| 5.0E−01 | 3.55E+00 | 0 | 3.721E−18 | 1.5 | 1 | 5 | 10 | 0.7 |
| 5.0E−01 | 3.09E+00 | 0 | 3.234E−18 | 1.5 | 1 | 5 | 10 | 0.725 |
| 5.0E−01 | 2.70E+00 | 0 | 2.824E−18 | 1.5 | 1 | 5 | 10 | 0.75 |
| 5.0E−01 | 2.36E+00 | 0 | 2.477E−18 | 1.5 | 1 | 5 | 10 | 0.775 |
| 5.0E−01 | 2.08E+00 | 0 | 2.181E−18 | 1.5 | 1 | 5 | 10 | 0.8 |

CHART 3-continued

| η (particle volume fraction) | $\alpha_{sca}$ (cm$^{-1}$) | Transmittance/mm | $C_{sca}$ (cm$^2$) | $n_p$ | $n_m$ | r (mm) | d (mm) | λ (μm) |
|---|---|---|---|---|---|---|---|---|
| 5.0E−01 | 1.84E+00 | 1.13E−280 | 1.929E−18 | 1.5 | 1 | 5 | 10 | 0.825 |
| 5.0E−01 | 2.67E+02 | 0 | 2.234E−15 | 1.5 | 1 | 10 | 20 | 0.4 |
| 5.0E−01 | 2.09E+02 | 0 | 1.753E−15 | 1.5 | 1 | 10 | 20 | 0.425 |
| 5.0E−01 | 1.66E+02 | 0 | 1.394E−15 | 1.5 | 1 | 10 | 20 | 0.45 |
| 5.0E−01 | 1.34E+02 | 0 | 1.123E−15 | 1.5 | 1 | 10 | 20 | 0.475 |
| 5.0E−01 | 1.09E+02 | 0 | 9.149E−16 | 1.5 | 1 | 10 | 20 | 0.5 |
| 5.0E−01 | 8.98E+01 | 0 | 7.527E−16 | 1.5 | 1 | 10 | 20 | 0.525 |
| 5.0E−01 | 7.46E+01 | 0 | 6.249E−16 | 1.5 | 1 | 10 | 20 | 0.55 |
| 5.0E−01 | 6.24E+01 | 0 | 5.231E−16 | 1.5 | 1 | 10 | 20 | 0.575 |
| 5.0E−01 | 5.27E+01 | 0 | 4.412E−16 | 1.5 | 1 | 10 | 20 | 0.6 |
| 5.0E−01 | 4.47E+01 | 0 | 3.747E−16 | 1.5 | 1 | 10 | 20 | 0.625 |
| 5.0E−01 | 3.82E+01 | 0 | 3.203E−16 | 1.5 | 1 | 10 | 20 | 0.65 |
| 5.0E−01 | 3.29E+01 | 0 | 2.754E−16 | 1.5 | 1 | 10 | 20 | 0.675 |
| 5.0E−01 | 2.84E+01 | 0 | 2.382E−16 | 1.5 | 1 | 10 | 20 | 0.7 |
| 5.0E−01 | 2.47E+01 | 0 | 2.070E−16 | 1.5 | 1 | 10 | 20 | 0.725 |
| 5.0E−01 | 2.16E+01 | 0 | 1.807E−16 | 1.5 | 1 | 10 | 20 | 0.75 |
| 5.0E−01 | 1.89E+01 | 0 | 1.585E−16 | 1.5 | 1 | 10 | 20 | 0.775 |
| 5.0E−01 | 1.67E+01 | 0 | 1.396E−16 | 1.5 | 1 | 10 | 20 | 0.8 |
| 5.0E−01 | 1.47E+01 | 0 | 1.234E−16 | 1.5 | 1 | 10 | 20 | 0.825 |

Figure 2:
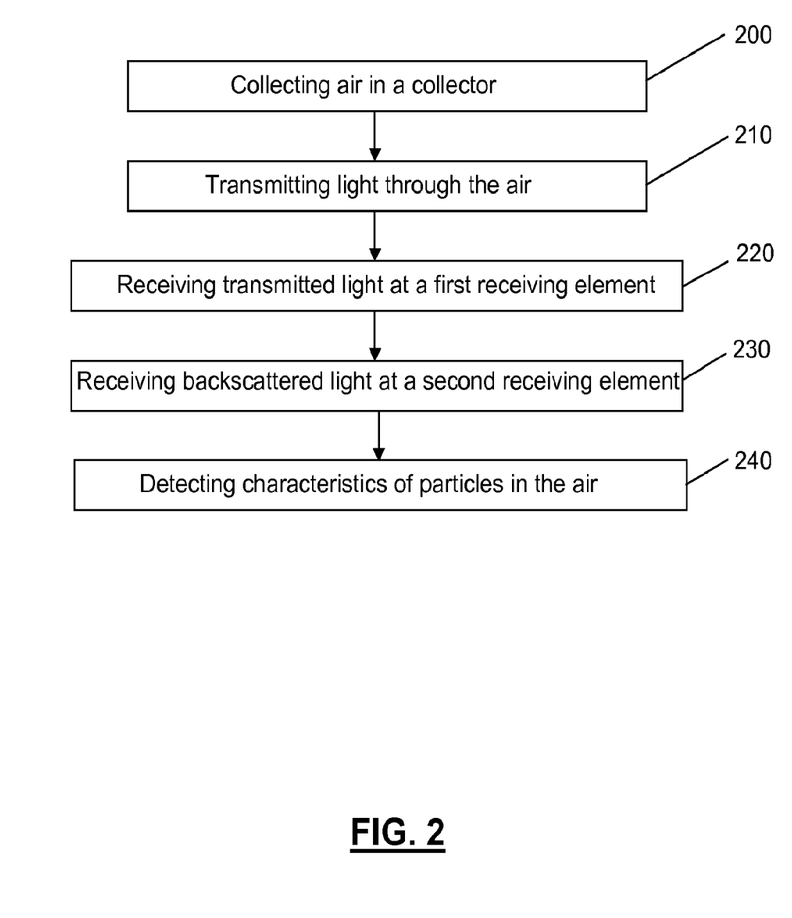
FIG. 2 depicts a method for measuring particles in air in accordance with an illustrative embodiment.

FIG. 2 depicts a method for measuring particles in air using nanoparticle monitoring device 100 of FIG. 1 in accordance with an illustrative embodiment. In an operation 200, air containing various particles is collected in a collector of a particle detector. In an operation 210, a light is transmitted through the collected air using a light source. Incident light that passes entirely through the collected air is received at a first light-receiving element, in an operation 220. At least a portion of the transmitted light is backscattered after it contacts the various particles in the collected air. In an operation 230, the backscattered light is received at a second light-receiving element. In illustrative embodiments, the intensity of the backscattered light may be increased using a lens, and the backscattered light may be captured by an optical fiber through which the backscattered light is transmitted to the second light-receiving element.

In an operation 240, various characteristics of the particles in the collected air are determined based on the amount of incident light and backscattered light received at the first and second light-receiving elements. These characteristics may include the sizes of the various particles in the collected air as well as the concentration of the particles. The sizes of the various particles are calculated based on the amount of backscattered light received at the second light-receiving element, and the concentration or volume fraction of the particles is determined based on the attenuation factor or transmittance of the transmitted light. These calculations are performed according to the Raleigh scattering model described above with reference to Eqns. 1 and 2. In an embodiment, the calculations are performed by a processor or other computing device that is configured to receive inputs from the first and second light-receiving elements. The processor or computing device is further configured to use the inputs from the first and second light-receiving elements to determine the amount of backscattered light and the attenuation factor of the transmitted light and to calculate the sizes and concentrations of the particles based on this information and based on Equations 1 and 2 described above.

Figure 3:
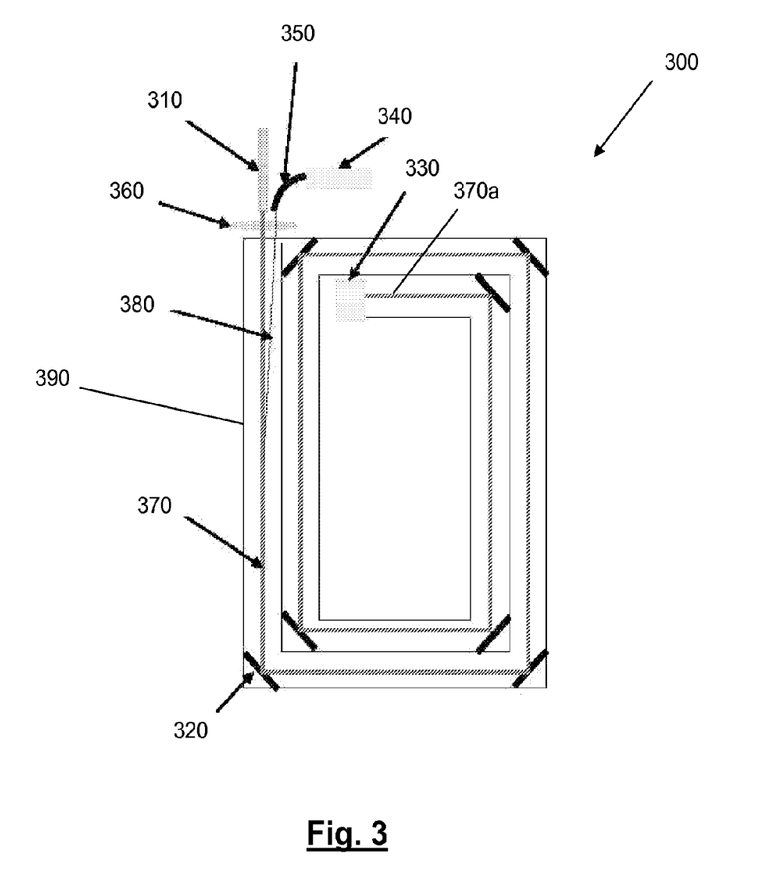
FIG. 3 depicts a nanoparticle monitoring device in accordance with an illustrative embodiment.

As discussed above, miniaturization of monitoring devices creates enhanced desirability for and applicability of such devices. As discussed above, with respect to FIG. 1, a light guiding distance must be long enough to enable sufficient measurement of transmitted light attenuation due to scattering by particles in the collected air. The smaller the particles being detected, the longer the light guiding distance that is required. Described below is an illustrative embodiment of a monitoring device that maximizes the light guiding distance while minimizing the overall size of the monitoring device. Maximization of the light guiding distance is achieved by circulating incident light inside the device using mirrors. FIG. 3 depicts a nanoparticle monitoring device 300 in accordance with such an illustrative embodiment.

Device 300 includes a light source 310 that is configured to transmit incident light 370 through a volume of air collected in a collector 390. In an embodiment, light source 310 is a semiconductor laser that outputs a light having a wavelength of 660 nm, 589 nm, 468 nm, 440 nm, or 405 nm. In alternative embodiments, light source 310 may produce light at alternative wavelengths and light source 310 may produce any kind of light that can retain its directionality. In one possible embodiment, a laser capable of emitting visible light may be used. For example, the laser may be a yttrium aluminum garnet (YAG) laser, a helium-neon (He—Ne) laser, an argon-ion laser, or any other semiconductor laser known to those of skill in the art.

Air may be moved into and out of the collector via any process or device known to those of skill in the art such a pump or a fan. For example, according to a first embodiment, a pump or a fan may be located near a first light receiving element 130 and may be configured to move air into and out of the device. According to such an embodiment, the pump or fan may be stopped when a measurement is being performed to maintain a constant number of particles within collector 120 during the measurement. In alternative embodiments, the measurements of the particles are done without stopping the pump or fan, thus allowing for real-time monitoring.

The air in collector 390 may include various particles. As incident light 370 is transmitted through the collected air in collector 390, some light 380 is backscattered as it contacts the various particles. Collector 390 provides a light guiding distance that is sufficient to enable the measurement of transmitted light attenuation due to scattering by the various particles in the collected air. Mirrors 320 increase the light guiding distance by reflecting incident light 370 along a light guiding path within the monitoring device. Mirrors 320 reflect incident light 370 along the light guiding path to a light-receiving element 330 located at an end of the light guiding path. In an embodiment, mirrors 320 may also reflect backscattered light 380 along the light guiding path back to light-receiving element 340. In an embodiment, a monitoring device with a volume of 80 cm$^3$ may provide a light guiding distance of about 3 meters by guiding the incident light path inward using several mirrors. Such an embodiment allows for the detection of particles having diameters on the order of nanometers. Alternative embodiments may employ greater or fewer mirrors to increase the light guiding distance as needed.

Light-receiving element 330 receives incident light 370 that successfully passes through the air in collector 390 along the entire light guiding path. As discussed above, light-receiving element 340 receives backscattered light 380. An optical fiber 350 may capture backscattered light 380 and provide an optical path by which backscattered light 380 is transmitted to light-receiving element 340. In an embodiment, light-receiving elements 330 and 340 comprise an avalanche photodiode or a charge-coupled device. Nanoparticle monitoring device 300 further includes a lens 360 that is configured to increase the intensity of backscattered light 380 prior to reception of the backscattered light at light-receiving element 340.

As light 370 is transmitted through the collected air, some of the light is backscattered (i.e., backscattered light 370) as it contacts the particles in the collected air. A portion of light 370 (i.e., incident light 370$a$) will successfully pass through the collected air to light-receiving element 330. The amount of incident light 370$a$ and backscattered light 380 received at light-receiving elements 330 and 340 is used to determine the sizes of the various particles within the collected air based on a dynamic light scattering profile determined from an amount of backscattered light 380, and to determine a concentration of the various particles based on an attenuation factor of incident light 370$a$. A Raleigh scattering model as described above with reference to Eqns. 1 and 2 is used to perform such calculations.

Figure 4:
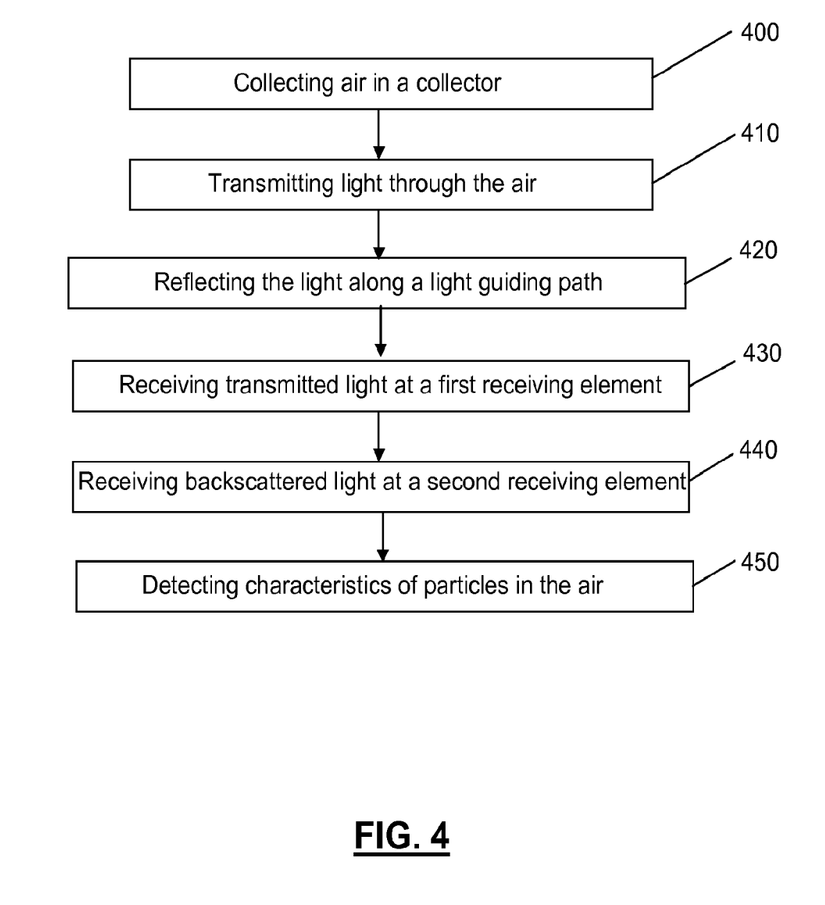
FIG. 4 depicts a method for measuring particles in air in accordance with an illustrative embodiment.

FIG. 4 depicts a method for measuring particles in air using the particle detector 300 of FIG. 3 in accordance with an illustrative embodiment. In an operation 400, air containing various particles is collected in a collector of particle detector 300. In an operation 410, a light is transmitted through the collected air using a light source. The light is reflected along a light guiding path using various mirrors, in an operation 420.

Incident light that passes along the light guiding path and entirely through the collected air is received at a first light-receiving element, in an operation 430. At least a portion of the transmitted light is backscattered after it contacts the various particles in the collected air. In an operation 440, the backscattered light is received at a second light-receiving element. In illustrative embodiments, the intensity of the backscattered light may be increased using a lens, and the backscattered light may be captured by an optical fiber through which the backscattered light is transmitted to the second light-receiving element.

In an operation 450, various characteristics of the particles in the collected air are determined based on the amount of incident light and backscattered light received at the first and second light-receiving elements. Theses characteristics may include the sizes of the various particles in the collected air as well as the concentration of the particles. The sizes of the various particles are calculated based on the amount of backscattered light received at the second light-receiving element, and the concentration of the particles is determined based on the attenuation factor of the transmitted light. These calculations are performed according to the Raleigh scattering model described above with reference to Eqns. 1 and 2.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method for optically detecting nanoparticles, the method comprising:
   collecting air in a nanoparticle collector;
   transmitting light through the air using a light source;
   receiving at least a portion of the transmitted light at a first light-receiving element;
   receiving backscattered light at a second light-receiving element;
   detecting, by a computing device, a size of one or more of the nanoparticles based on the backscattered light; and
   detecting, by the computing device, a concentration of the nanoparticles based on an attenuation factor of the transmitted light.

2. The method of claim 1, further comprising increasing the intensity of the backscattered light using a lens, and wherein the lens is disposed between the nanoparticle collector and the first light-receiving element.

3. The method of claim 1, further comprising passing the transmitted light along a light guiding path between the light source and the first light-receiving element by reflecting the transmitted light off of two or more mirrors.

4. The method of claim 1, further comprising passing the air from an ambient environment outside the nanoparticle collector into the nanoparticle collector.

5. The method of claim 1, further comprising capturing the backscattered light in an optical fiber and transmitting the backscattered light from the nanoparticle detector to the first light-receiving element using the optical fiber.

6. The method of claim 1, wherein the attenuation factor is determined based at least in part on a length of the nanoparticle collector.

7. The method of claim 6, wherein the nanoparticle collector comprises two or more mirrors to reflect the transmitted light along a light guiding path such that the direction of the light guiding path is changed at each mirror.

8. The method of claim 7, wherein the light guiding path extends one or more times around a central point.

9. A nanoparticle detector comprising:
   a nanoparticle collector configured to collect a volume of air that includes nanoparticles;
   a light source configured to transmit light through the volume of air;
   a first light-receiving element configured to receive at least a portion of the transmitted light and detect scattering properties of the transmitted light;
   a second light-receiving element configured to receive backscattered light; and
   a processor configured to detect a size of one or more of the nanoparticles based on the backscattered light and detect a concentration of the nanoparticles based on an attenuation factor of the at least a portion of the transmitted light received at the first light-receiving element.

10. The nanoparticle detector of claim 9, further comprising a lens configured to increase the intensity of the backscattered light, wherein the lens is disposed between the nanoparticle collector and the first light-receiving element.

11. The nanoparticle detector of claim 9, further comprising an optical fiber disposed between the nanoparticle detector and the first light-receiving element, wherein the optical fiber is configured to capture the backscattered light and transmit the backscattered light to the first light-receiving element.

12. The nanoparticle detector of claim 9, wherein the size of the one or more nanoparticles is determined according to a dynamic light scattering profile that is based on the backscattered light.

13. The nanoparticle detector of claim 9, wherein the light source is a semiconductor laser, and wherein the first light-receiving element is an avalanche photodiode or a charge-coupled device.

14. The nanoparticle detector of claim 9, wherein the nanoparticle collector comprises two or more mirrors configured to reflect the transmitted light along a light guiding path.

15. The nanoparticle detector of claim 14, wherein the nanoparticle collector comprises a channel that extends one or more times around a central point, and wherein the light guiding path passes through the nanoparticle collector as it extends the one or more times around the central point.

16. The nanoparticle detector of claim 15, wherein the attenuation factor is determined based at least in part on a length of the nanoparticle collector.

17. The nanoparticle detector of claim 15, wherein the two or more mirrors are configured to reflect the transmitted light along a light guiding path such that the direction of the light guiding path is changed at each mirror.

18. The nanoparticle detector of claim 15, wherein the light guiding path has a length of greater than 2.5 meters and extends entirely within the nanoparticle collector, and wherein the nanoparticle collector is arranged within a volume of less than 80 cubic centimeters.

19. The nanoparticle detector of claim 14, further comprising a device configured to move the air from an ambient environment outside the nanoparticle detector into the nanoparticle collector.

20. A nanoparticle detector comprising:
   a nanoparticle collector configured to collect a volume of air that includes nanoparticles, wherein the nanoparticle collector comprises a spiral configuration such that a channel of the nanoparticle collector wraps one or more times around a central point, and wherein the channel of the nanoparticle collector has a first end and a second end;
   a light source configured to transmit light from the first end of the channel of the nanoparticle collector through the volume of air;
   a first light-receiving element positioned at the second end of the channel of the nanoparticle collector and configured to receive at least a portion of the transmitted light and detect scattering properties of the transmitted light;
   a second light-receiving element configured to receive backscattered light; and
   a processor configured to, based on a Raleigh scattering model, detect a size of one or more of the nanoparticles based on the backscattered light and detect a concentration of the nanoparticles based on an attenuation factor of the at least a portion of the transmitted light received at the first light- receiving element.

* * * * *

UNITED STATES PATENT AND TRADEMARK OFFICE
CERTIFICATE OF CORRECTION

PATENT NO. : 8,441,636 B2
APPLICATION NO. : 13/201124
DATED : May 14, 2013
INVENTOR(S) : Fukui It is certified that error appears in the above-identified patent and that said Letters Patent is hereby corrected as shown below:

On the Title Page, in item (56), under "OTHER PUBLICATIONS", in Column 2, Line 7, delete "x38118,xml?pf=true&ArticleID=x38118)," and insert -- x36118.xml?pf=true&ArticleID=x36118), --, therefor.

Title Page 2, in item (56), under "OTHER PUBLICATIONS", in Column 1, Line 2, delete "MEasurement" and insert -- Measurement --, therefor.

Title Page 2, in item (56), under "OTHER PUBLICATIONS", in Column 2, Line 1, delete "=en&st=" and insert -- =en&sl= --, therefor.

In the Specification

In Column 3, Lines 13-14, delete "a yttrium" and insert -- an yttrium --, therefor.

In Column 10, Line 39, delete "a yttrium" and insert -- an yttrium --, therefor.

In Column 11, Line 20, delete "backscattered light 370)" and insert -- backscattered light 380) --, therefor.

In Column 11, Line 55, delete "Theses" and insert -- These --, therefor.

In the Claims

In Column 15, Line 3, in Claim 20, delete "light- receiving" and insert -- light-receiving --, therefor.

Signed and Sealed this
Twenty-seventh Day of August, 2013

Teresa Stanek Rea
*Acting Director of the United States Patent and Trademark Office*